United States Patent [19]

Molinari

[11] Patent Number: 5,091,540
[45] Date of Patent: Feb. 25, 1992

[54] PROCESS FOR PREPARING CLOTRIMAZOLE

[75] Inventor: Egidio Molinari, Longone Al Segrino, Italy

[73] Assignee: Erregierre Industria Chimica S.P.A., Milan, Italy

[21] Appl. No.: 500,134

[22] Filed: Mar. 28, 1990

[30] Foreign Application Priority Data

Dec. 29, 1989 [IT] Italy ................................ 22875 A/89

[51] Int. Cl.$^5$ ........................................... C07D 233/54
[52] U.S. Cl. .................................................... 548/341
[58] Field of Search ........................................ 548/341

[56] References Cited

U.S. PATENT DOCUMENTS 2,215,862  9/1940  Waldmann et al. ................ 548/341
3,929,820  12/1975  Buchel ............................... 548/341

Primary Examiner—Mary C. Lee
Assistant Examiner—Robert C. Whittenbaugh
Attorney, Agent, or Firm—Birch, Stewart, Kolasch & Birch

[57] ABSTRACT

A process for preparing clotrimazole by reacting 2-chlorotriphenylmethylchloride with imidazole in a hydrocarbon solution in the presence of a neutralizing agent, followed by nitration of the product obtained. The nitrate is reconverted into the free base with caustic alkali.

3 Claims, No Drawings

PROCESS FOR PREPARING CLOTRIMAZOLE

This invention relates to the preparation of clotrimazole.

Clotrimazole, i.e. 1-(o.Cl-α,α-diphenylbenzyl)imidazole, of formula:

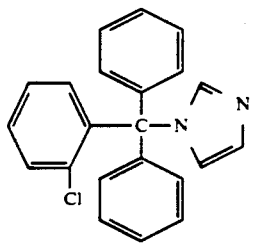

is a known antimycotic for human use, and a fungicide useful against plant pathogenic fungi.

Methods for its preparation are described in various patents. In particular, U.S. Pat. No. 3,929,820 describes a process starting from chlorophenyldiphenyl methylchloride and imidazole in the presence of a neutralizing agent, such as triethylamine, in a polar organic solvent. The process is strictly limited by the use, as the medium for the reaction in question, of a solvent falling within the given definition, i.e. having a dielectric constant of at least 4.5 and preferably between 15 and 50. In all the examples of the implementation of the process according to the patent in question, acetonitrile (D=37.5) is used as solvent.

Using a solvent having a dielectric constant within the preferred range results in particularly high yields.

In one specific example, starting from p-chlorophenyldiphenylmethylchloride and imidazole in acetonitrile, a pure product yield, of M.P. 140° C., is given as 71% of the theoretical.

According to the present invention we have now discovered a process which enables clotrimazole to be prepared from o.chlorobenzotrichloride via 2-chlorotriphenylmethylchloride, and reacting this with imidazole operating in hydrocarbon solvents, such as benzene, of low dielectric constant to obtain the desired product at high purity with high yield.

The process consists essentially of the following steps:

a) reacting o.chlorobenzotrichloride with benzene in the presence of aluminium trichloride to obtain 2-chlorotriphenyl-methylchloride;

b) reacting the product obtained in a) with imidazole in benzene in the presence of an amine, such as triethylamine;

c) precipitating the product in the form of nitrate to purify it;

d) converting the product of c) into the free base, which is crystallized from acetone.

The process is illustrated in greater detail by the following example.

EXAMPLE 900 g of benzene and 117.5 g of aluminium chloride are placed in a 2 liter flask fitted with a reflux condenser, stirrer and drying tube.

The mixture is cooled to 0° C. and a solution of 150 g of o.chlorobenzotrichloride in 150 g of benzene is added while maintaining a temperature not exceeding 15° C. The mixture is heated carefully under reflux for 4 hours. HCl is evolved.

The reaction mixture is then cooled to ambient temperature and slowly poured into 300 g of concentrated hydrochloric acid and 800 g of ice, so as not to exceed 25° C. The aqueous layer is then separated and discarded.

The benzene solution is washed with a solution of 230 g of sodium chloride in 800 g of water. The benzene phase is separated and dried over anhydrous sodium sulphate for 1 hour, and then filtered.

45 g of imidazole in 70 g of triethylamine are added to the filtrate and the mixture heated for 3 hours at 45°-50° C. It is then cooled to ambient temperature and 500 g of water are added while stirring. The aqueous layer is separated and discarded, and the benzene phase washed with 200 g of water. The benzene layer is separated and evaporated to dryness under vacuum.

The residue is dissolved in 250 g of ethyl acetate while stirring. 250 g of water are added and the solution titrated to calculate the exact quantity of nitric acid to add.

The solution is cooled to 15° C. and the calculated nitric acid quantity is quickly added. Stirring is halted when precipitation commences, and the system left until precipitation is complete.

The product is centrifuged and washed with 300 g of ethyl acetate and then with 300 g of water.

The moist product is placed into the reaction flask and 300 g of water, 450 g of methylene chloride, 5 g of triethylamine and 110 g of 30% sodium hydroxide are added. The mixture is stirred until a solution forms and the solution then left until the phases separate.

The aqueous phase is washed with 100 g of methylene chloride, and the pooled organic phases are washed twice with 200 g of water each time.

The solution in methylene chloride is treated with YMS decolorizing carbon and filtered, the filter then being washed with methylene chloride which si recovered by distillation. The residue is taken up in 100 g of acetone and redistilled to completely eliminate the methylene chloride.

The residue is taken up in 900 g of acetone and heated to 50° C. to obtain a complete solution. YMS decolorizing carbon and triethylamine are added, the mixture filtered and washed with acetone. Part of the acetone is then removed by distillation, reducing the volume to about 500 c.c. The mixture is cooled to 0° C. and, after five hours, the product is centrifuged and washed with 100 g of acetone. It is dried at 60° C., to obtain 150 g of final product.

I claim:

1. A process for preparing clotrimazole, i.e. 1-(o.Cl-α, α-diphenylbenzyl)imidazole, from chlorobenzotrichloride and imidazole, consisting essentially of the following steps:

a) reacting o.chlorobenzotrichloride with benzene in the presence of aluminium trichloride;

b) reacting the 2-chlorotriphenylmethylchloride obtained in a) with imidazole in a hydrocarbon solution in the presence of an amine;

c) nitrating the product obtained in b) in solution with concentrated nitric acid;

d) converting the nitration product into the free base by reaction with a caustic alkali;

e) purifying the solution obtained in d) and recovering the desired product by distilling the solvent and crystallizing.

2. A process as claimed in claim 1, wherein step b) is conducted in a benzene solution.

3. A process as claimed in claim 1, wherein the neutralizing agent used in step b) is an aliphatic amine.

* * * * *